(12) United States Patent
Stout et al.

(10) Patent No.: US 8,641,675 B2
(45) Date of Patent: Feb. 4, 2014

(54) SYSTEMS AND METHODS FOR PREVENTING SEPTUM DAMAGE IN AN INTRAVASCULAR DEVICE

(75) Inventors: Marty L. Stout, South Jordan, UT (US); Shaun Staley, Sandy, UT (US); Weston F. Harding, Lehi, UT (US); Ralph L. Sonderegger, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 297 days.

(21) Appl. No.: 13/042,143

(22) Filed: Mar. 7, 2011

(65) Prior Publication Data

US 2012/0232499 A1    Sep. 13, 2012

(51) Int. Cl.
 A61M 5/178    (2006.01)
 A61M 5/14    (2006.01)

(52) U.S. Cl.
 USPC ............ 604/167.02; 604/167.01; 604/167.03; 604/167.04; 604/168.01; 604/256

(58) Field of Classification Search
 USPC .......... 604/117, 167.01–167.04, 164.07, 256, 604/272–274, 168.01, 263, 110, 192, 198
 See application file for complete search history.

(56) References Cited

U.S. PATENT DOCUMENTS

| | | | |
|---|---|---|---|
| 4,387,879 A | 6/1983 | Tauschinski | |
| 4,449,693 A | 5/1984 | Gereg | |
| 4,525,157 A * | 6/1985 | Vaillancourt | 604/510 |
| 4,758,225 A | 7/1988 | Cox et al. | |
| 4,842,591 A | 6/1989 | Luther | |
| 4,874,377 A | 10/1989 | Newgard et al. | |
| 4,917,668 A | 4/1990 | Haindl | |
| 4,935,010 A | 6/1990 | Cox et al. | |
| 5,041,097 A | 8/1991 | Johnson | |
| 5,053,014 A | 10/1991 | Van Heugten | |
| 5,062,836 A | 11/1991 | Wendell | |
| 5,064,416 A | 11/1991 | Newgard et al. | |
| 5,084,023 A | 1/1992 | Lemieux | |
| 5,085,645 A | 2/1992 | Purdy et al. | |
| 5,108,374 A | 4/1992 | Lemieux | |
| 5,127,905 A | 7/1992 | Lemieux | |
| 5,154,703 A | 10/1992 | Bonaldo | |
| 5,156,596 A | 10/1992 | Balbierz et al. | |
| 5,234,410 A | 8/1993 | Graham et al. | |
| 5,295,969 A | 3/1994 | Fischell et al. | |

(Continued)

FOREIGN PATENT DOCUMENTS

| | | |
|---|---|---|
| CA | 2133053 A1 | 3/1995 |
| WO | WO 99/34849 | 7/1999 |
| WO | WO 2004/032995 A2 | 4/2004 |
| WO | WO 2010/093791 A1 | 8/2010 |

OTHER PUBLICATIONS

Silva, Elson, Email Regarding "Respecting Hydrology Science and IP Rights—US Pat. Application 20110130728," pp. 1-6, Jun. 2, 2011.

*Primary Examiner* — Bhisma Mehta
*Assistant Examiner* — Lauren M Peng
(74) *Attorney, Agent, or Firm* — Jeanne Lukasavage; Craig Metcalf; Kirton McConkie (57) ABSTRACT

Systems and methods to provide an intravenous device having flashback capabilities and features to permit a flashback notch of an introducer needle to bypass a septum of the device without incurring an undesirable contact between the flashback notch of the introducer needle and a related contact surface of the septum.

12 Claims, 12 Drawing Sheets

(56) References Cited

U.S. PATENT DOCUMENTS

| | | | |
|---|---|---|---|
| 5,330,435 A | 7/1994 | Vaillancourt | |
| 5,342,315 A | 8/1994 | Rowe et al. | |
| 5,350,363 A | 9/1994 | Goode et al. | |
| 5,352,205 A | 10/1994 | Dales et al. | |
| 5,356,381 A * | 10/1994 | Ensminger et al. | 604/288.03 |
| 5,405,323 A | 4/1995 | Rogers et al. | |
| 5,456,675 A | 10/1995 | Wolbring et al. | |
| 5,487,728 A | 1/1996 | Vaillancourt | |
| 5,520,666 A | 5/1996 | Choudhury et al. | |
| 5,549,566 A | 8/1996 | Elias et al. | |
| 5,549,577 A | 8/1996 | Siegel et al. | |
| 5,575,769 A | 11/1996 | Vaillancourt | |
| 5,613,663 A | 3/1997 | Schmidt et al. | |
| 5,651,772 A | 7/1997 | Arnett | |
| 5,657,963 A | 8/1997 | Hinchliffe et al. | |
| 5,697,915 A | 12/1997 | Lynn | |
| 5,738,144 A | 4/1998 | Rogers | |
| 5,749,861 A | 5/1998 | Guala et al. | |
| 5,806,831 A | 9/1998 | Paradis | |
| 5,817,069 A | 10/1998 | Arnett | |
| 5,911,710 A | 6/1999 | Barry et al. | |
| 5,954,698 A | 9/1999 | Pike | |
| 5,967,490 A | 10/1999 | Pike | |
| 6,039,302 A | 3/2000 | Cote, Sr. et al. | |
| 6,077,244 A | 6/2000 | Botich et al. | |
| 6,117,108 A | 9/2000 | Woehr et al. | |
| 6,171,287 B1 | 1/2001 | Lynn et al. | |
| 6,273,869 B1 | 8/2001 | Vaillancourt | |
| 6,485,473 B1 | 11/2002 | Lynn | |
| 6,565,542 B2 * | 5/2003 | Kumar et al. | 604/264 |
| 6,575,960 B2 | 6/2003 | Becker et al. | |
| 6,595,981 B2 | 7/2003 | Huet | |
| 6,699,221 B2 * | 3/2004 | Vaillancourt | 604/167.01 |
| 6,740,063 B2 | 5/2004 | Lynn | |
| 6,883,778 B1 | 4/2005 | Newton et al. | |
| 7,008,404 B2 | 3/2006 | Nakajima | |
| 7,347,839 B2 | 3/2008 | Hiejima | |
| 7,396,346 B2 | 7/2008 | Nakajima | |
| 7,470,254 B2 | 12/2008 | Basta et al. | |
| 7,736,339 B2 | 6/2010 | Woehr et al. | |
| 7,914,494 B2 | 3/2011 | Hiejima | |
| 2007/0083162 A1 | 4/2007 | O'Reagan et al. | |
| 2008/0039796 A1 | 2/2008 | Nakajima | |
| 2008/0108944 A1 | 5/2008 | Woehr et al. | |
| 2010/0204675 A1 | 8/2010 | Woehr et al. | |

\* cited by examiner

SYSTEMS AND METHODS FOR PREVENTING SEPTUM DAMAGE IN AN INTRAVASCULAR DEVICE

BACKGROUND OF THE INVENTION

This present invention relates generally to cannulae and associated methods. More specifically, this disclosure discusses a cannula or needle having a flashback notch that is configured to bypass a septum of an intravascular device without incurring septum damage, preventing proper retraction and shielding of the needle, and/or providing a disconcerting feel to the clinician. Further, the disclosure discusses methods for aligning various features of the needle and the septum to minimize and/or prevent damage to the septum.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of intravascular access devices. Over-the-needle peripheral IV catheters are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter. Moreover, the catheter and needle are often assembled so that during insertion, the bevel of the needle faces up, away from the patient's skin. The catheter and introducer needle are generally inserted at a shallow angle through the patient's skin into a blood vessel.

In order to verify proper placement of the needle and/or the catheter in the blood vessel, the operator generally confirms that there is a "flashback" of blood into a flashback chamber associated with the needle assembly. Flashback generally entails the appearance of a small amount of blood, which exits the needle through an aperture or notch which is visible within the needle assembly or between the needle and the transparent catheter.

The operator may then withdraw the introducer needle from the catheter. In some cases, the intravascular device further includes an internal septum having a slit or opening through which the introducer needle passes. The septum generally provides a fluid tight seal around a cross-section of the introducer needle. The septum is positioned within the intravascular device so as to provide a fluid barrier that prevents undesirable exposure to blood during and after the catheterization process. Following insertion of the cannula or catheter, the introducer needle is withdrawn from the intravascular device, whereby the "flashback" aperture or notch must pass through the slit in the septum. As the notch is typically provided by removing a portion of the needle's wall, the septum can engage or snag on a distal edge of the notch as the introducer needle is retracted past the septum. This engagement can prevent proper retraction and shielding of the needle, be disconcerting to the clinician, or even damage the septum.

Thus, while methods currently exist for incorporating a septum into an intravascular device having flashback capability, challenges still exist. Accordingly, it would be an improvement in the art to augment or even replace current techniques with other techniques.

BRIEF SUMMARY OF THE INVENTION

This present invention relates generally to cannulae and associated methods. More specifically, this disclosure discusses a cannula or needle having a flashback notch that is configured to bypass a septum of an intravascular device without incurring septum damage, preventing proper retraction and shielding of the needle, and/or providing a disconcerting feel to the clinician. Further, the disclosure discusses methods for aligning various features of the needle and the septum to minimize and/or prevent damage to the septum.

In some implementations of the present invention, an intravascular device is provided comprising a catheter adapter having an inner surface and an outer surface, wherein a septum is seated within the inner surface of the catheter adapter and includes an opening defined by a plurality of flaps or leaves, each leaf having a contact surface. The intravascular device further includes a notch for providing a flashback signal to indicate proper insertion of the introducer needle into the vasculature of a patient. Still further, in some implementations a width and/or length of the notch is configured to be less than a width of the contact surface of the leaf, such that the contact surface of the leaf is incapable of substantially penetrating the notch. For example, in some implementations an axial length of the notch is shorter than a related contact surface of the leaf. Further, in some implementations a circumferential width of the notch is narrower that the related contact surface of the leaf.

In some implementations, an intravascular device is provided comprising a septum having at least three leaves, each leaf having an apex which contacts an outer surface of the introducer needle. In some implementations, the septum is oriented within a catheter adapter of the intravascular device such that the notch of the needle, or cannula and the apex are misaligned. In other implementations, the notch comprises a plurality of notches or holes, wherein the apex of each leaf contacts a portion of the outer surface of the needle which is interposed between the plurality of notches.

In some implementations, a needle feature is provided having a width greater than an outer diameter of the needle, the needle feature forming a portion of an outer surface of the needle and being positioned between the notch and a tip of the cannula. In other implementations, an intravenous device is provided comprising a notch shield having an inner diameter greater than the outer diameter of the needle and less than the width of the needle feature, such that a portion of the needle feature binds on a distal surface of the needle shield. The notch shield is further positioned within the opening of the septum, wherein the notch shield further includes an opening though which a shaft portion of the needle or cannula is slidably positioned, wherein upon withdrawing the needle in a proximal direction, the notch is drawn into the notch shield, whereafter the needle feature contacts a distal surface of the notch shield thereby displacing the notch shield from the opening of the septum in a proximal direction.

In some implementations, an intravascular device is providing which includes a catheter adapter having an inner surface and an outer surface, a septum seated within the inner surface of the catheter adapter thereby dividing a lumen of the catheter adapter into a proximal chamber and a distal chamber, the septum having an opening defined by a plurality of leaves, and the needle having a notch for providing a flashback signal. In some implementation, the intravascular device further includes a feature for preventing a portion of the plurality of leaves from substantially penetrating the notch. For example, in some implementations the feature comprises a contact surface of each of the septum having a width that is greater than a width of the notch. Further, in some implementations the feature comprises a misaligned position of the notch relative to a misaligned position of an apex surface of the septum. Still further, in some implementations the feature comprises a notch shield positioned within an opening of the septum.

Some implementations of the present invention include a method for preventing septum damage in an intravascular device, assisting in proper retraction and shielding of the needle, and/or eliminating a disconcerting feel to the clinician, wherein the method includes the steps of providing a catheter adapter having an inner surface and an outer surface, seating a septum within the inner surface of the catheter adapter thereby dividing a lumen of the catheter adapter into a proximal chamber and a distal chamber, the septum having an opening defined by a plurality of leaves, providing a cannula having a notch for providing a flashback signal, and providing a feature for preventing a portion of the plurality of leaves from substantially penetrating the notch. Further, in some implementations the method includes a step for misaligning a position of the notch relative to a position of the apex.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the accompanying Figures, could be arranged and designed in a wide variety of different configurations. Thus, the following more detailed description of some embodiments of the invention, as represented in the Figures, is not intended to limit the scope of the invention, as claimed, but is merely representative of some presently preferred embodiments of the invention.

Figure 1:
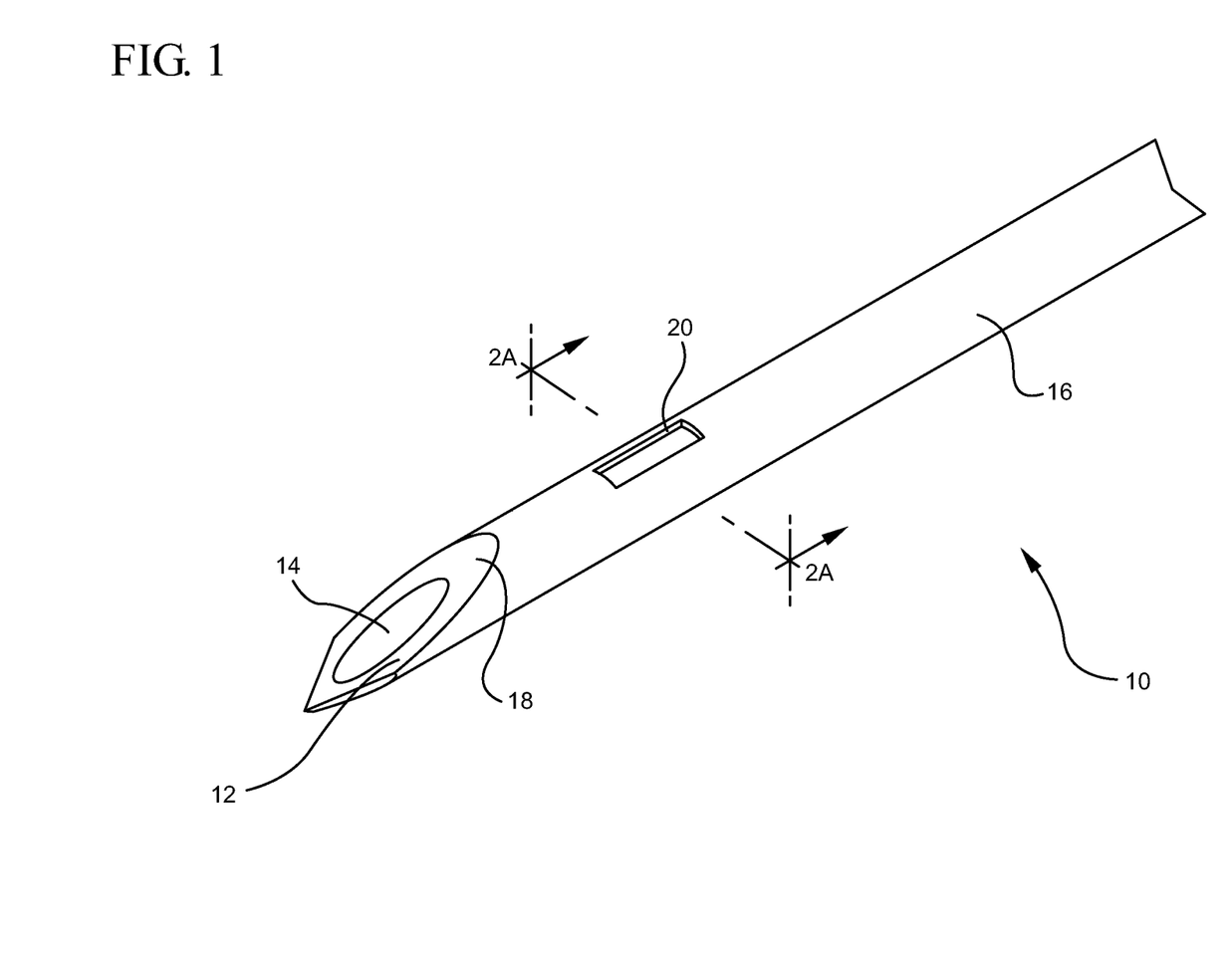
FIG. 1 illustrates a perspective view of a representative embodiment of a cannula comprising a notch feature in accordance with a representative embodiment of the present invention.

Generally, this disclosure discusses a cannula or introducer needle having a notch feature for providing a flashback communication indicating proper insertion of an intravascular device into the vascular system of a patient. While the described cannula can comprise any suitable component or characteristic, FIG. 1 illustrates a representative embodiment in which the cannula (e.g., needle 10) comprises a notch feature 20, described below in greater detail.

Cannula 10 may comprise virtually any rigid tube that both includes a sharpened distal tip and which is configured to puncture an animal's body, to access an intended space, and to draw off or to introduce fluid from or into the intended space. One example of a suitable cannula comprises a venipuncture needle. In this example, the venipuncture needle may include virtually any suitable venipuncture needle, including an introducer needle for use in an IV catheter assembly (e.g., an over-the-needle peripheral IV catheter assembly), a venous needle, an arterial needle, and the like. For simplicity, however, the cannula 10 with notch feature 20 is described below with reference to an introducer needle.

The introducer needle 10 may have any component that is suitable for use with an IV catheter assembly. For instance, FIG. 1 shows a representative embodiment in which the introducer needle 10 comprises a sharpened distal tip 12, an inner lumen 14, and an elongated tubular shaft 16. Moreover, each component of the needle may have any suitable characteristic. For example, the distal tip of the needle may comprise a standard bevel, a short bevel, a true short bevel, a bias grind point, a vet point, a lancet point, a deflected point (anticoring), or another suitable known or novel needle point. Additionally, the lumen and elongated tubular shaft may be any suitable size. For example, the needle may be any suitable length or any suitable gauge (e.g., from about a 7 to about a 33 on the Stubs scale) that allows it to be used as the introducer needle in an intravascular device assembly.

As mentioned above, needle 10 also defines a notch feature 20 which provides fluid communication between inner lumen 14 and an exterior environment of needle 10. This notch feature may serve several purposes, including acting as an aperture through which blood can exit the inner lumen 14 of the needle 10 to provide flashback confirmation when the needle 10 is properly placed in a patient's vasculature.

The notch feature may have any orientation with respect to the needle's bevel that allows the notch feature to fulfill its intended purposes. In some embodiments, the notch feature is defined in the cannula so as to be offset in orientation from the direction in which the needle's bevel faces. In some instances in which the notch feature is defined in the needle so as to be offset from the direction of the bevel, the notch feature may allow for faster flashback confirmation in instances in which the user's line of sight includes the side of the needle in which the notch is defined but does not include the side of the needle from which the bevel faces. In other embodiments, the notch feature 20 is defined in the needle 10 so as to face in substantially the same direction as the needle's bevel 18, as illustrated.

Where the notch feature is offset from the direction of the needle's bevel, the notch feature can be offset in any suitable manner. For instance, the notch feature can be defined in the needle so as to face in an opposite direction to, a perpendicular direction to, or in another suitable direction with respect to the direction in which needle's bevel faces.

Figure 2A:
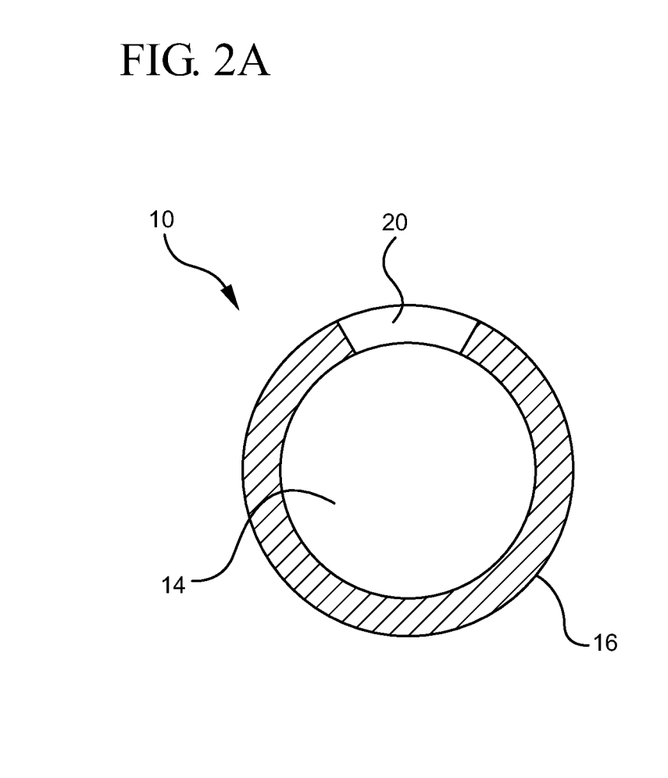
FIG. 2A illustrates a cross-section view of a notch feature of a cannula in accordance with a representative embodiment of the present invention.

The notch feature can have any suitable characteristic that allows it to provide the needle with flashback confirmation. In some embodiments, from a face view of the notch feature, the notch feature 20 comprises any suitable shape, including a shape that is substantially elliptical, square, rectangular, triangular, circular, polygonyl, irregular, etc. For instance, FIG. 2A illustrates an embodiment in which the notch feature 20 is substantially rectangular. In another example of a suitable characteristic, the notch feature may remove any amount of a cross-sectional area of the needle's sidewall that allows the notch feature to provide the needle with flashback confirmation while still allowing the cannula feature to have sufficient structural integrity to fulfill its intended purposes.

Figure 2B:
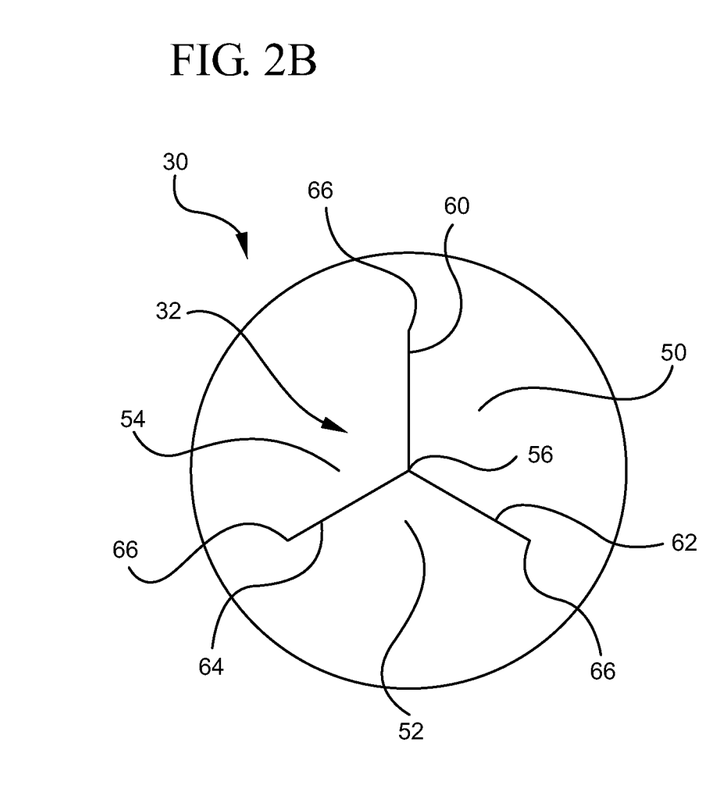
FIG. 2B illustrates a front plan view of a septum having a tri-leaf slit in accordance with a representative embodiment of the present invention.
Figure 3:
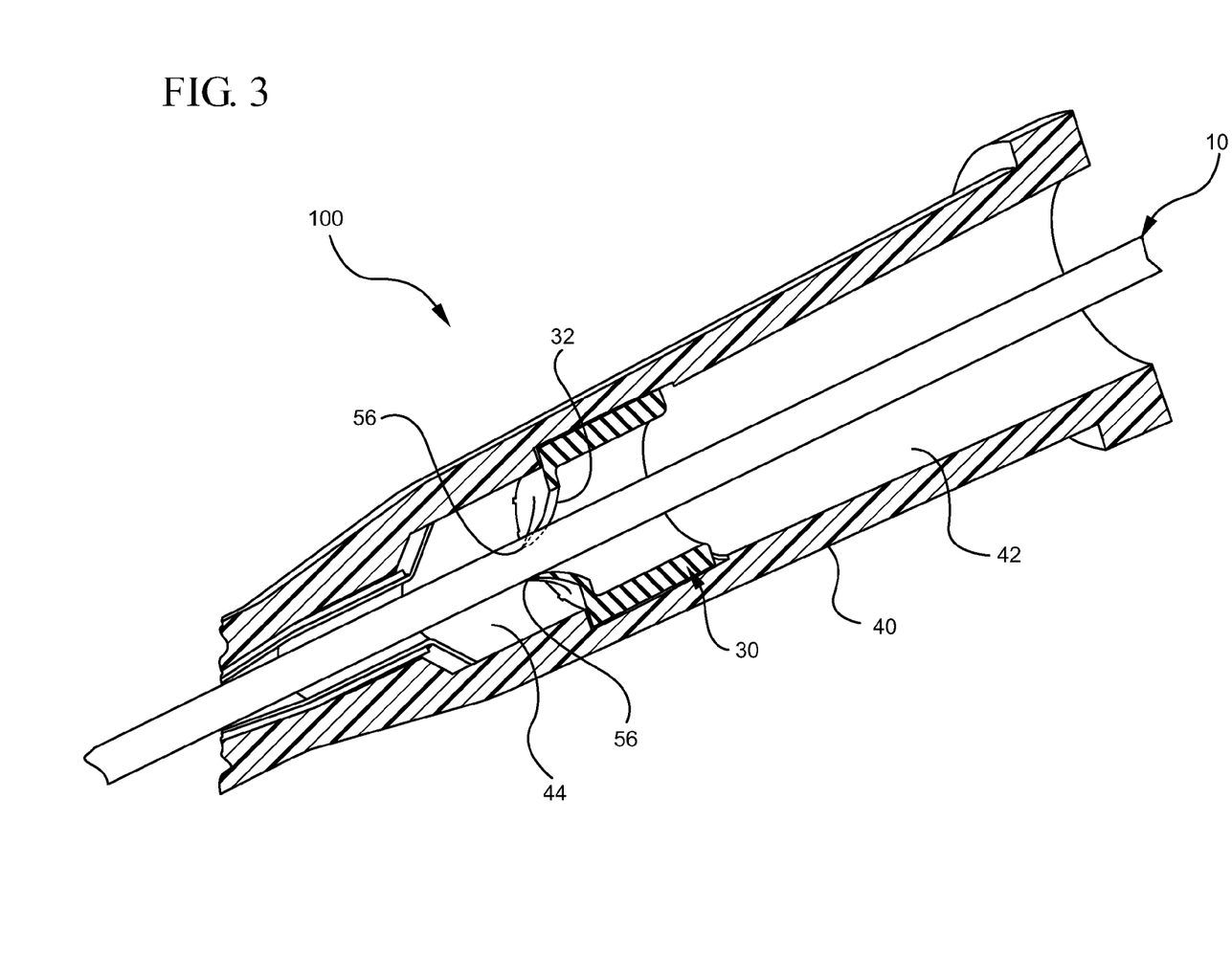
FIG. 3 illustrates a cross-section perspective view of an intravascular device in accordance with a representative embodiment of the present invention.

Referring now to FIGS. 2B and 3, in some embodiments an introducer needle 10 is used in combination with a septum 30. Septum 30 generally comprises a polymer membrane which is disposed within a catheter adapter 40 of an intravascular device 100. For example, in some embodiments septum 30 is positioned within catheter adapter 40 so as to divide an inner lumen of catheter adapter 40 into a proximal chamber 42 and a distal chamber 44. Accordingly, septum 30 acts as a blood barrier to control and/or isolate blood flow between the proximal and distal chambers 42 and 44.

In some embodiments, septum 30 further comprises an opening or slit 32 to accommodate passage of introducer needle 10. Slit 32 may include any shape or configuration to permit passage of needle 10. In some embodiments, slit 32 is provided by advancing the sharpened distal tip 12 of needle 10 through septum 30, whereby the distal tip 12 creates an opening in the septum 30. In other embodiments, septum 30 is manufactured to include a slit 32 configured to permit passage of needle 10. Further, in some embodiments slit 32 provides a fluid tight seal between septum 30 and an outer surface of needle 10. As such, when needle 10 is positioned within septum 30, blood flow from the distal chamber 44 to the proximal chamber 42 is prevented.

In some embodiments, septum 30 comprises a tri-leaf slit, wherein slit 32 provides three septum flaps or leaves 50, 52 and 54. For example, in some embodiments slit 32 comprises three slits or branches 60, 62 and 64 that are spaced approximately 120° apart. Branches 60, 62 and 64 each comprise a corner 66. Further, each leaf 50, 52 and 54 comprises an apex 56, the positions of which form a center of the slit 32.

In general, leaves 50, 52 and 54 of slit 32 are biased into an opened or expanded position by the interposed presence of elongated tubular shaft 16 of needle 10. As previously mentioned, in some embodiments leaves 50, 52 and 54 maintain a close tolerance with the outer surface of tubular shaft 16, thereby providing a fluid tight seal between septum 30 and needle 10.

Figure 4:
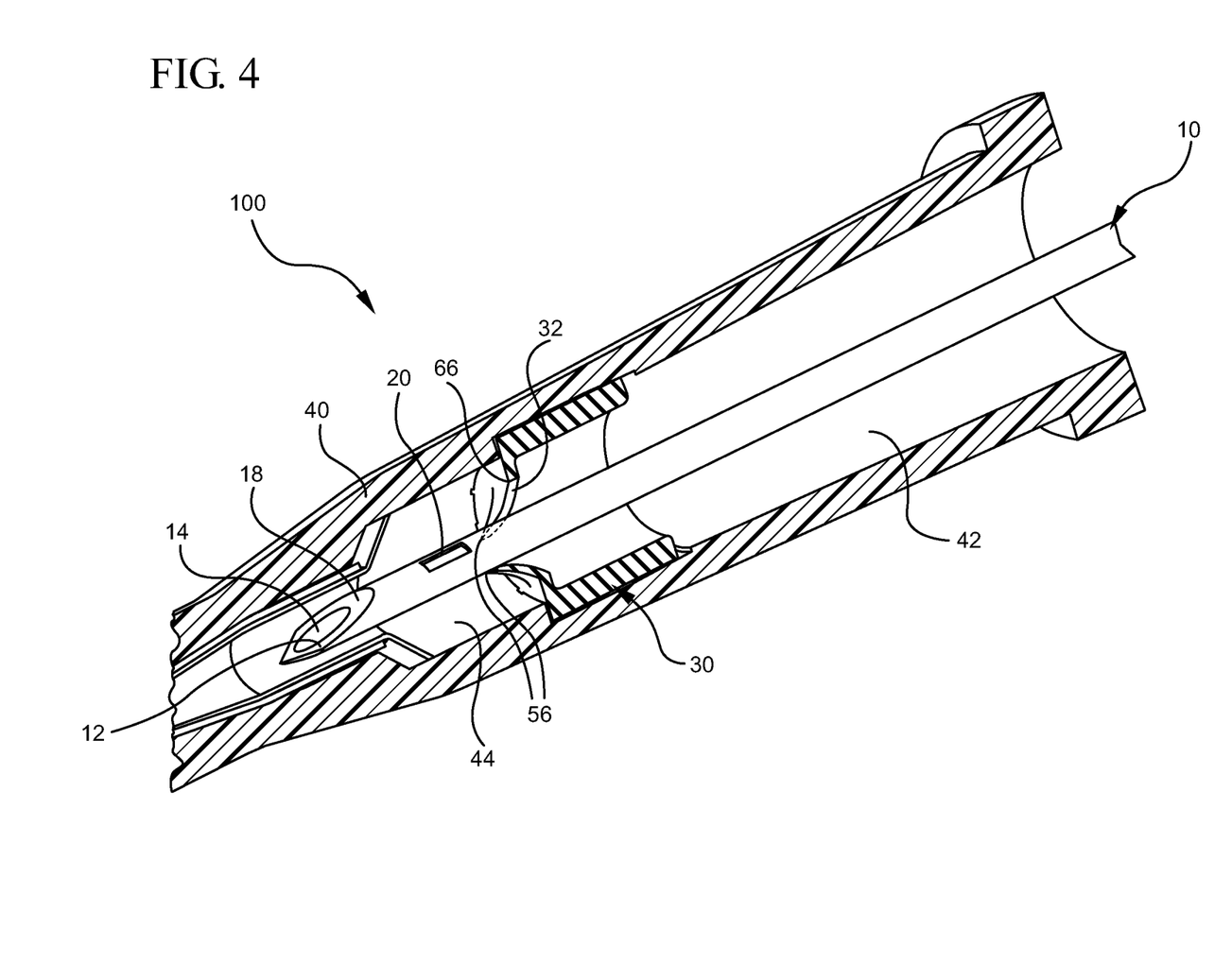
FIG. 4 illustrates a cross-section perspective view of an intravascular device and partially withdrawn introducer needle in accordance with a representative embodiment of the present invention.
Figure 5:
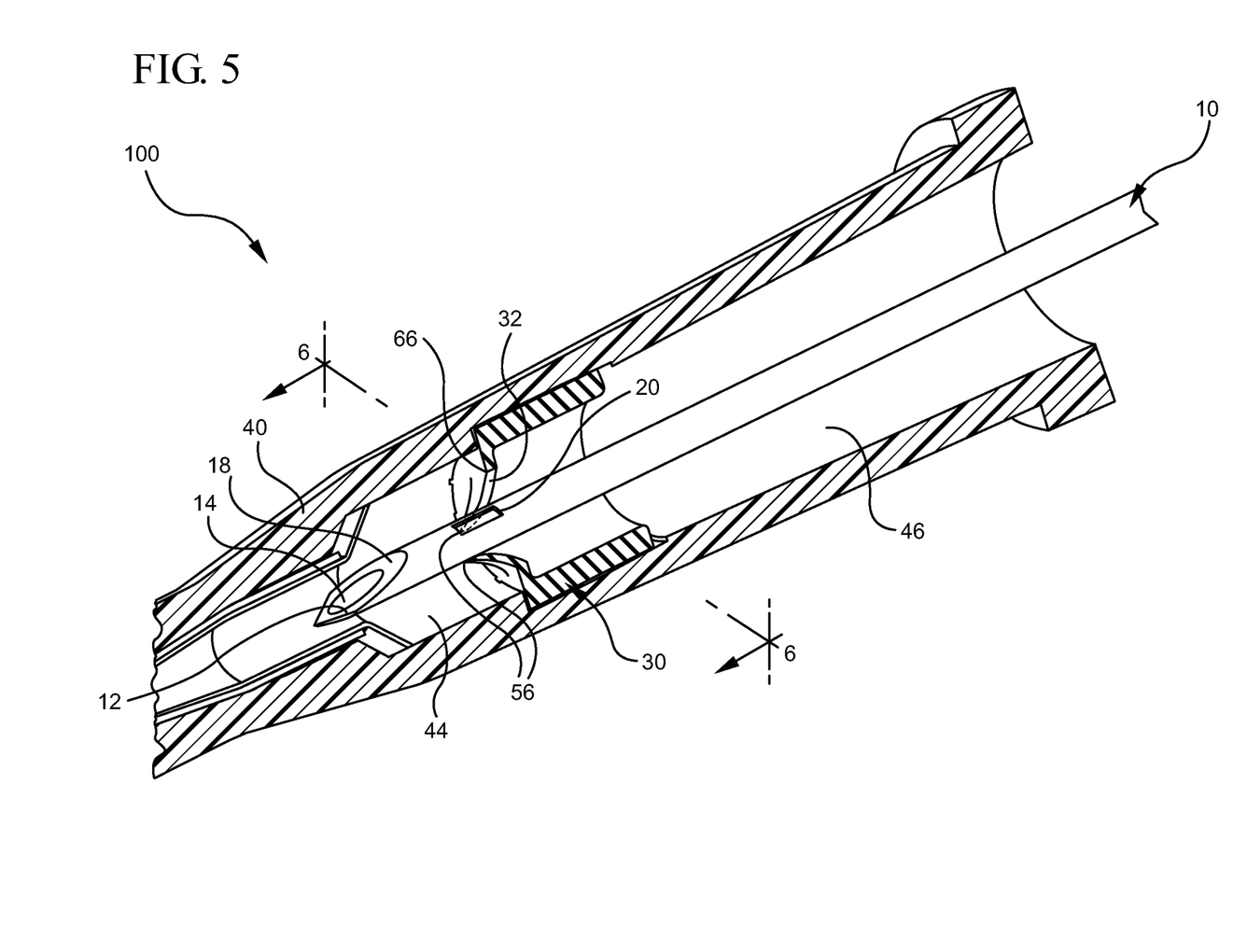
FIG. 5 illustrates a cross-section perspective view of an intravascular device and partially withdrawn introducer needle, wherein a notch feature of the introducer needle is positioned within a tri-leaf slit of a septum in accordance with a representative embodiment of the present invention.
Figure 6:
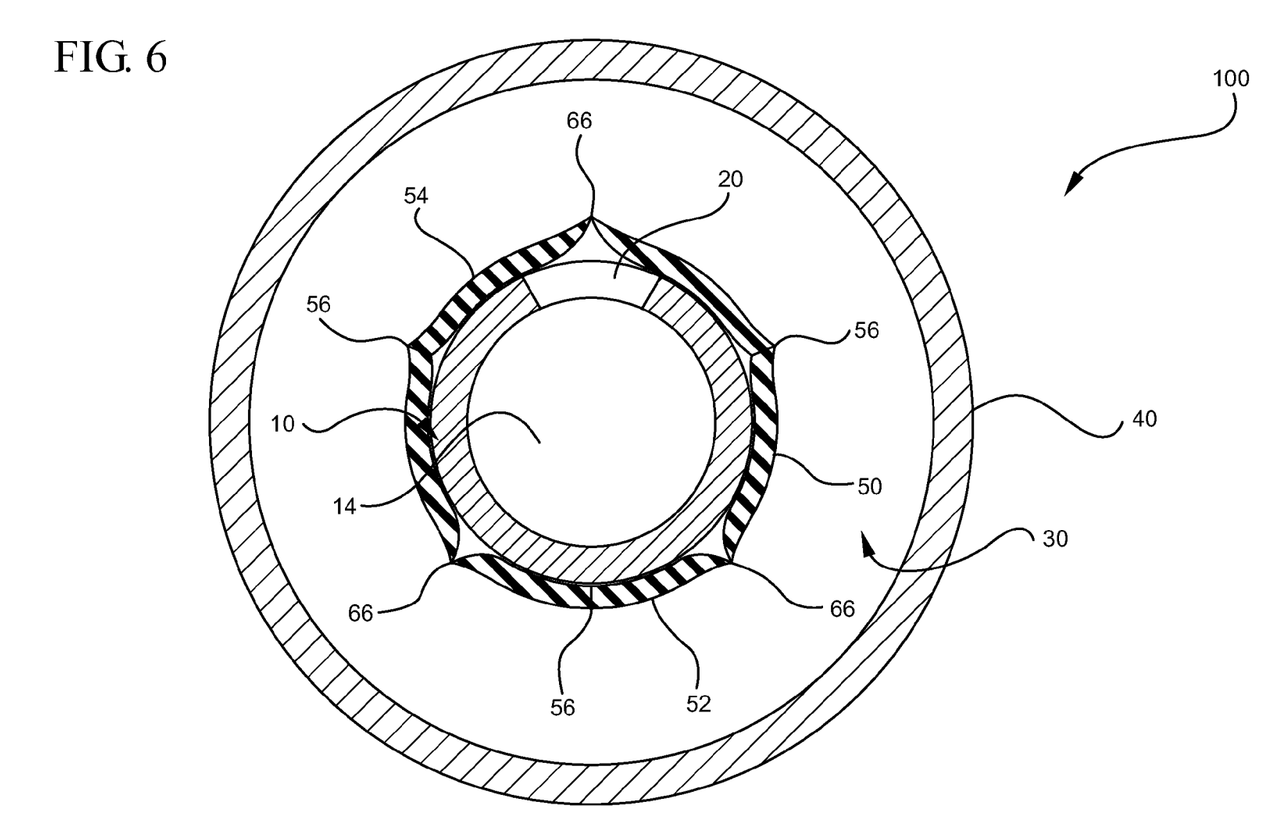
FIG. 6 is a cross-section distal view of an intravascular device and partially withdrawn introducer needle, wherein a notch feature of the introducer needle is positioned within a tri-leaf slit of a septum in accordance with a representative embodiment of the present invention.

Following insertion of the intravascular device 100 into a patient, introducer needle 10 is withdrawn from the device 100, as shown in FIG. 4. In some embodiments, the axial orientation of septum 30, as positioned within catheter adapter 40, is rotated such that notch feature 20 is in axial alignment with a corner 66 of tri-leaf slit 32, as shown in FIGS. 5 and 6. In other words, in some embodiments a feature is provided wherein the axial orientation of septum 30, as positioned within catheter adapter 40, is rotated such that notch feature 20 is misaligned with apexes 56 of flaps 50, 52 and 54. Accordingly, as notch feature 20 is withdrawn through slit 32, apexes 56 are axially positioned approximately 60° from notch feature 20, thereby preventing apexes 56 from entering into, or catching on notch feature 20. As such, needle 10 is able to be removed from intravascular device 100 without damaging the septum 30. Further, some embodiments of the present invention permit proper retraction and shielding of needle 10 by eliminating any undesirable interactions between notch feature 20 and septum 30. Still further, some embodiments of the present invention eliminate any disconcerting feelings that the clinician may feel through needle 10 as a result of an undesirable interaction between notch feature 20 and septum 30.

Figure 7:
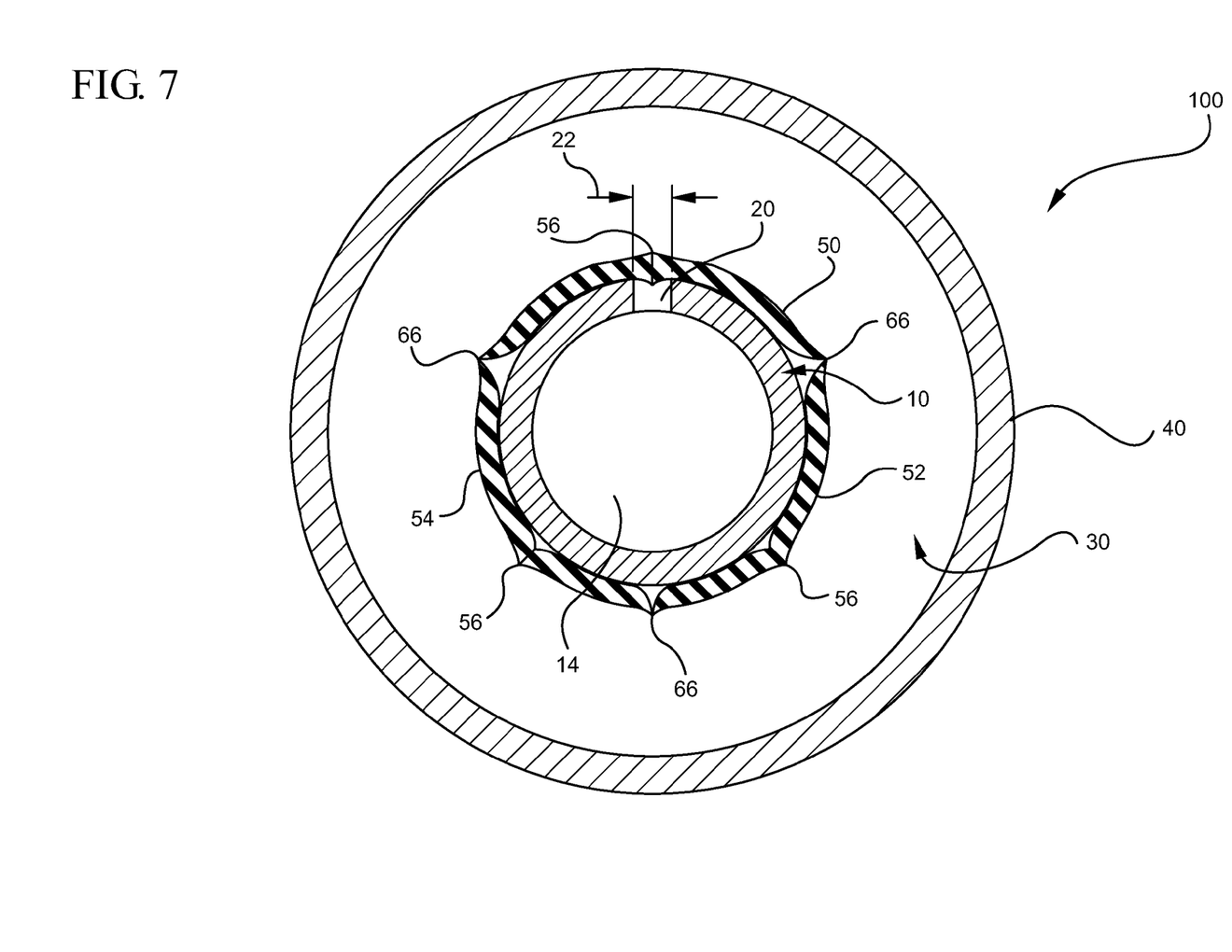
FIG. 7 is a cross-section distal view of an intravascular device and partially withdrawn introducer needle, wherein a notch feature of the introducer needle is positioned within a tri-leaf slit of a septum in accordance with a representative embodiment of the present invention.

In some embodiments, notches 20 comprises a plurality of small notches having sufficient size to still allow blood flow and visualization by the clinician, yet be small enough to prevent an undesirable interaction between the notches and a surface of the septum 30. Referring now to FIG. 7, in some embodiments a feature is provided wherein the axial orientation of septum 30, as positioned within catheter adapter 40, is rotated such that notch feature 20 is in axial alignment with an apex 56 of leaf 50. Accordingly, in some embodiments a width 22 of notch feature 20 is decreased so as to minimize the amount of apex 56 capable of entering notch feature 20.

Figure 8:
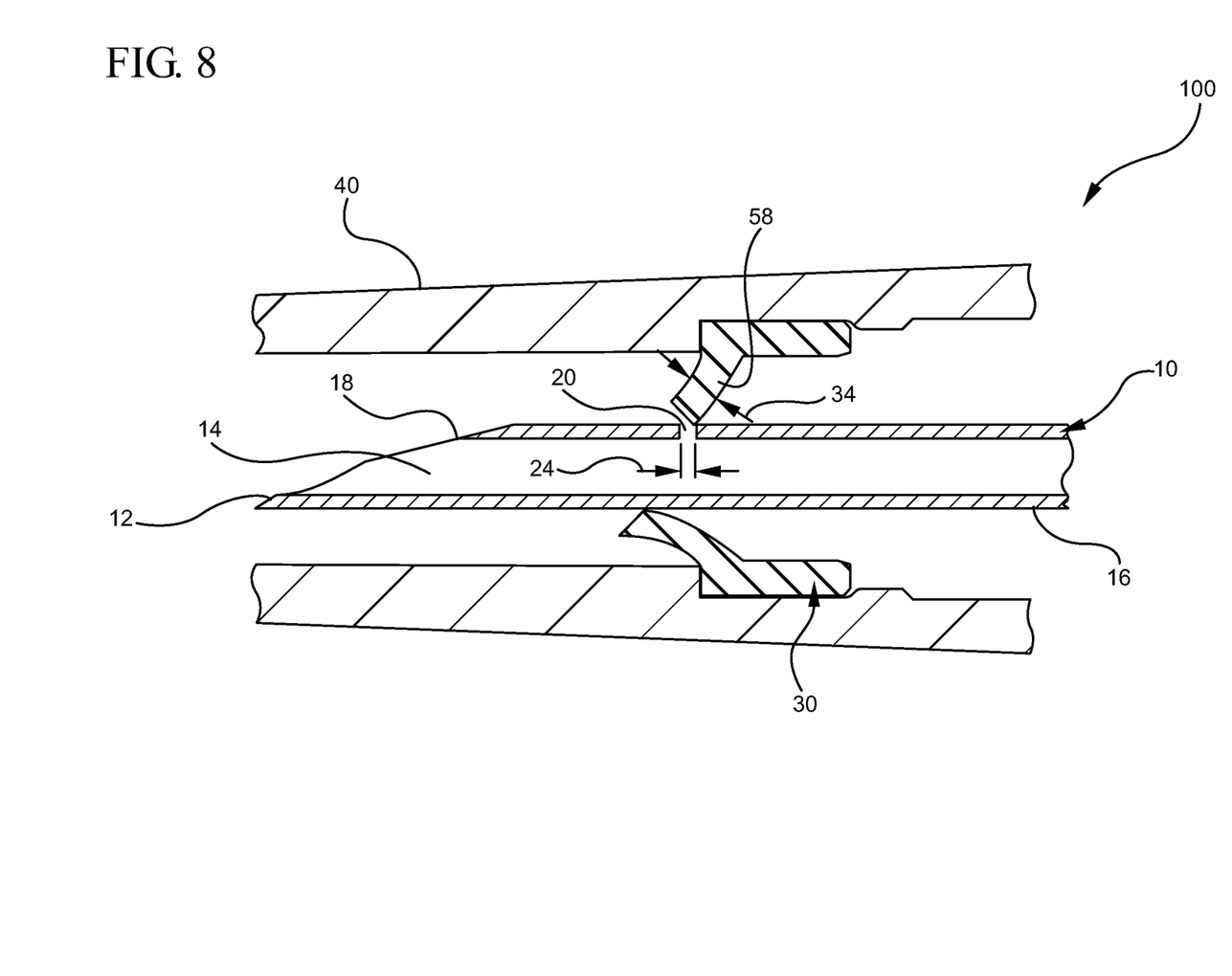
FIG. 8 is a cross-section side view of an intravascular device and partially withdrawn introducer needle, wherein a notch feature of the introducer needle is positioned within a tri-leaf slit of a septum in accordance with a representative embodiment of the present invention.

Further, in some embodiments a length 24 of notch feature 20 is configured to be less than a thickness 34 of flap 58, as shown in FIG. 8. As such, the thickness 34 of flap 58 prevents substantial penetration of flap 58 into notch feature 20, thereby avoiding any of the aforementioned undesirable interactions between notch feature 20 and septum 30. For example, in some embodiments a width and/or length 24 of notch 20 is configured to be less than a width 34 of a contact surface of the leaf 58, such that the contact surface of the leaf 58 is incapable of substantially penetrating the notch 20. In some embodiments, width 24 comprises an axial length of the notch 20, wherein the axial length is shorter than a related contact surface of leaf 58. As such, the contact surface of leaf 58 is prevented from substantially penetrating notch 20. Further, in some embodiments width 24 comprises a circumferential width of the notch 20, wherein the circumferential width is narrower that the related contact surface of leaf 58. As such, the contact surface of leaf 58 is prevented from substantially penetrating notch 20. Still further, in some embodiments width and/or length 24 comprises a surface area of notch 20, wherein the surface area of notch 20 is less than a surface area of the related contact surface of leaf 58. As such, the related contact surface of leaf 58 is prevented from substantially penetrating notch 20 thereby eliminating any undesirable contact between notch 20 and septum 30, as discussed previously.

The various notches of the present invention may be provided by any technique known in the art, including mechanical grinding, Electro-Chemical Grinding (ECG), laser oblation, and Electrical Discharge Machining (EDM). In some embodiments, notch features are provided which comprise different geometry and patterns for a notch or notches. For example, in some embodiments a laser, water jet, or similar technology is used to produce one or more small holes in the wall of the needle, thereby preventing septum leaf engagement while providing improved structural integrity and/or blood flow visualization when compared to a single large mechanical, ECG or EDM notch, as discussed below.

Figure 9:
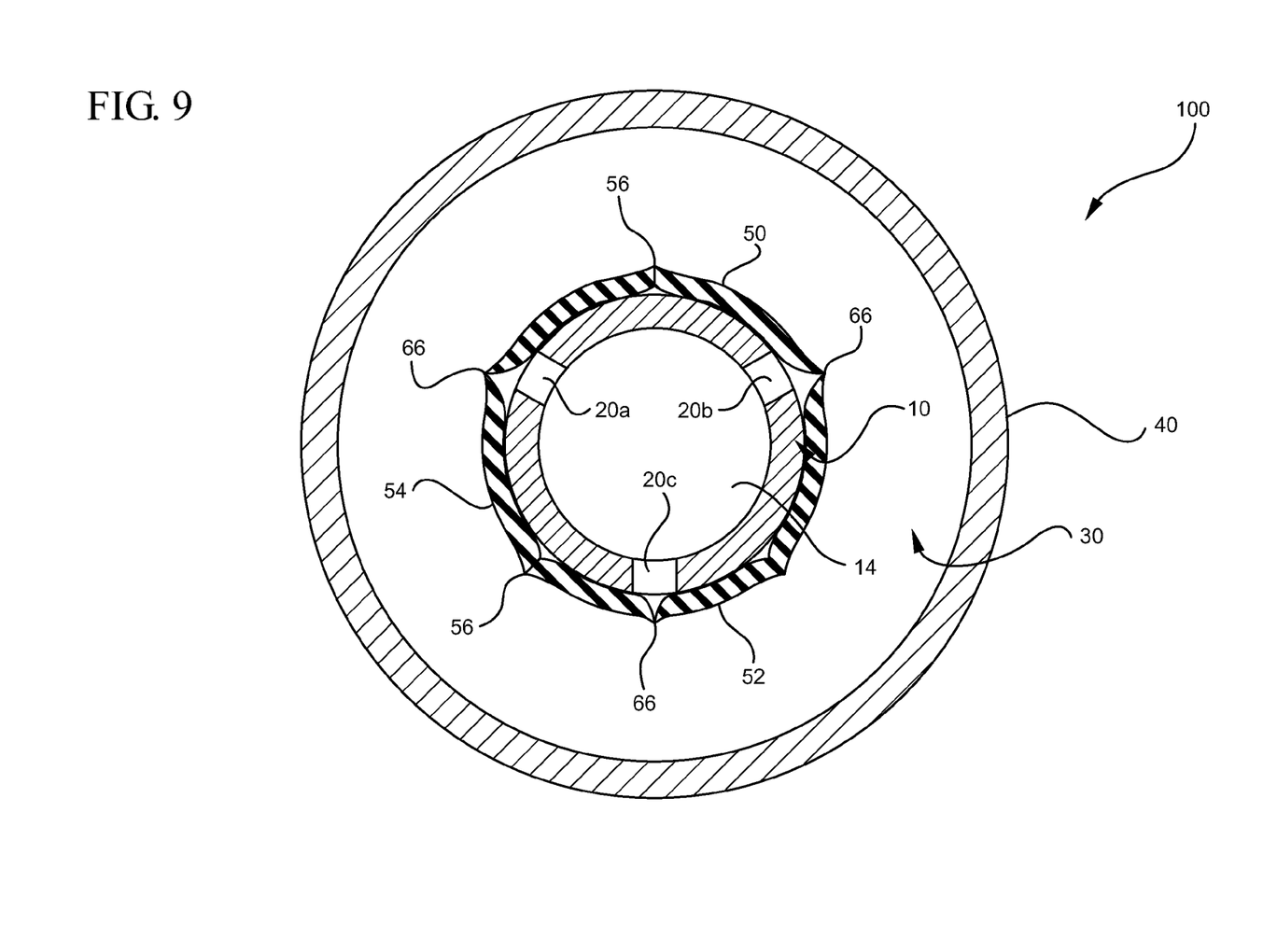
FIG. 9 is a cross-section distal view of an intravascular device and partially withdrawn introducer needle, wherein multiple notch features of the introducer needle are positioned within a tri-leaf slit of a septum in accordance with a representative embodiment of the present invention.

Referring now to FIG. 9, in some embodiments introducer needle 10 further comprises multiple notch features 20a, 20b, and 20c. Accordingly, in some embodiments intravascular device 100 comprises a feature wherein the axial orientation of septum 30, as positioned within catheter adapter 40, is rotated such that notch features 20a, 20b, and 20c are axially aligned with corners 66. Accordingly, as notch features 20a, 20b, and 20c are withdrawn through slit 32, apexes 56 are axially positioned approximately 60° from notch features 20a, 20b and 20c thereby preventing apexes 56 from entering into, or catching on the notch features.

Figure 10:
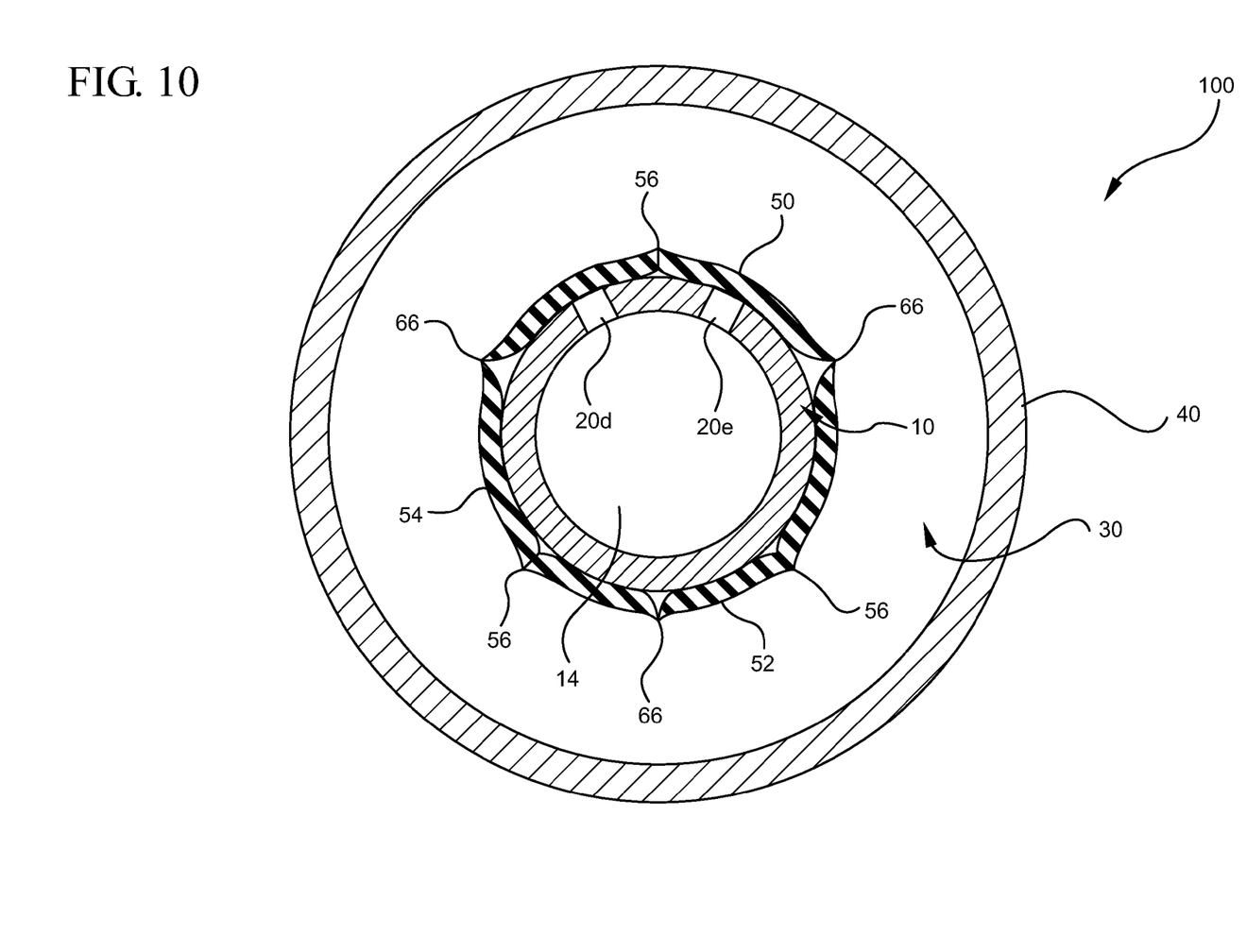
FIG. 10 is a cross-section distal view of an intravascular device and partially withdrawn introducer needle, wherein multiple notch features of the introducer needle are positioned within a tri-leaf slit of a septum in accordance with a representative embodiment of the present invention.

With reference to FIG. 10, in some embodiments introducer needle 10 further comprises multiple notch features 20d and 20e. Accordingly, in some embodiments intravascular device 100 comprises a feature wherein the axial orientation of septum 30, as positioned within catheter adapter 40, is rotated such that notch features 20d and 20e are axially misaligned with apex 56 of leaf 50. Accordingly, as notch features 20d and 20e are withdrawn through slit 32, apex 56 is axially positioned between notch features 20d and 20e thereby preventing any portion of apex 56 from entering into, or catching on the notch features.

Figure 11:
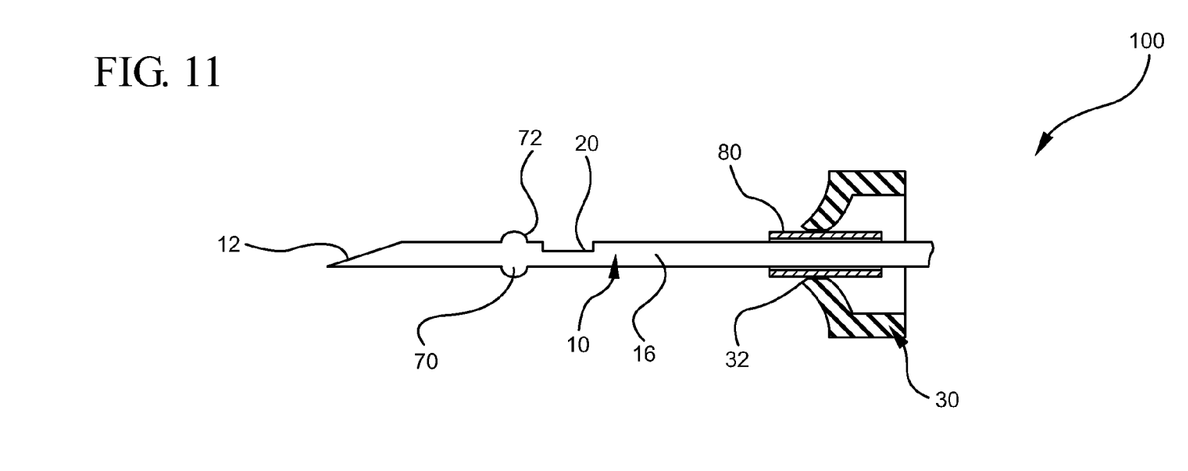
FIG. 11 is a cross-section side view of an intravascular device having a notch shield in accordance with a representative embodiment of the present invention.
Figure 12:
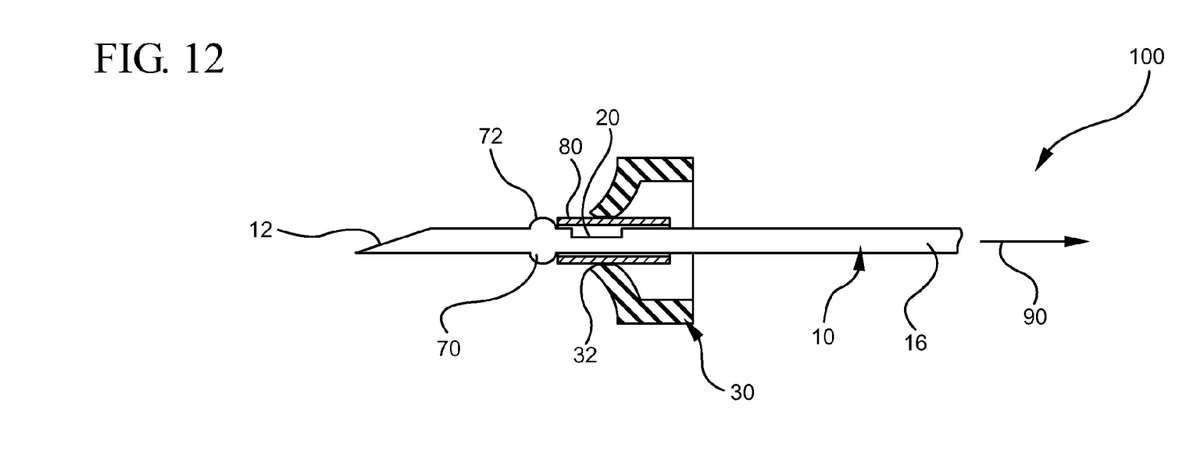
FIG. 12 is a cross-section side view of an intravascular device having a notch shield, wherein a notch feature of the introducer needle is positioned within the notch shield in accordance with a representative embodiment of the present invention.
Figure 13:
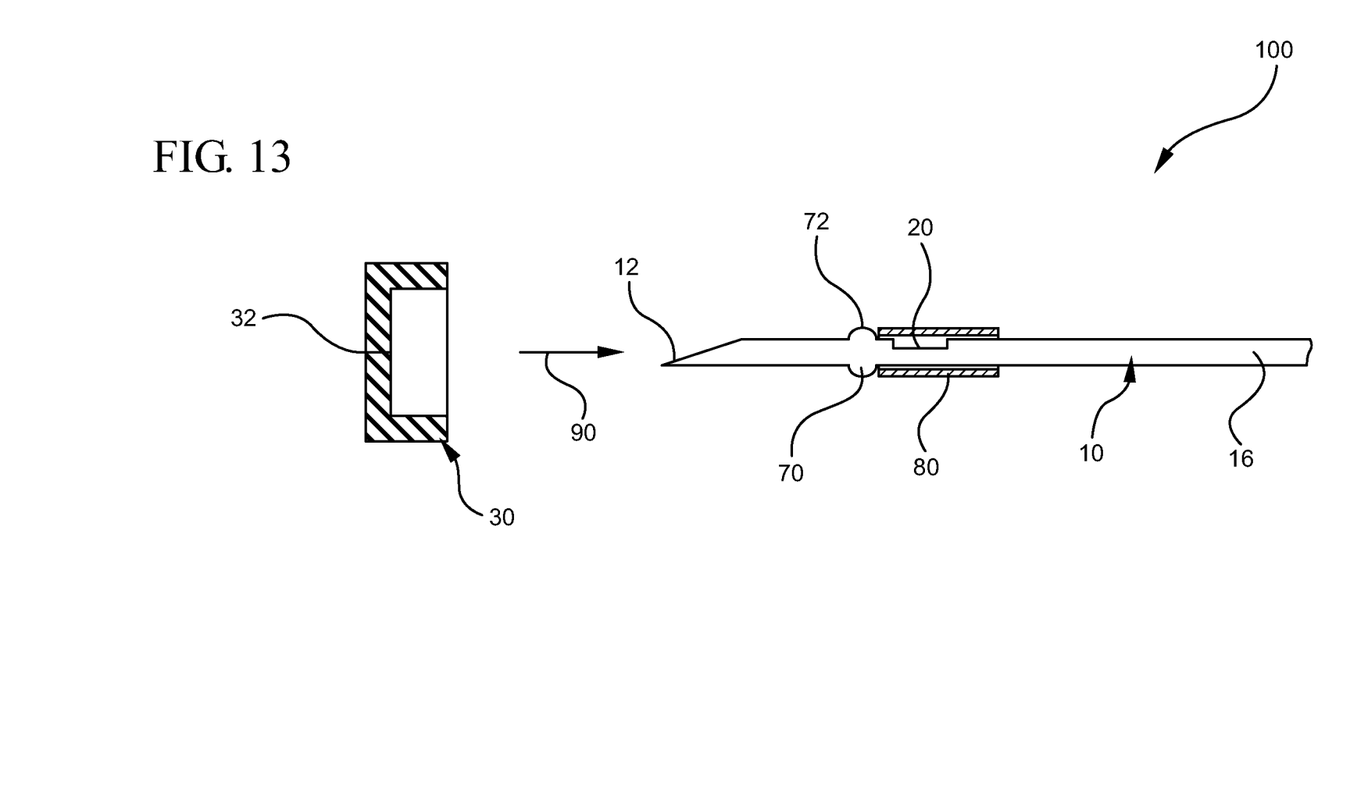
FIG. 13 is a cross-section side view of an intravascular device following removal of the introducer needle and notch shield in accordance with a representative embodiment of the present invention.

In some embodiments, introducer needle 10 further comprises a needle feature 70, as shown in FIGS. 11-13. Needle feature 70 may serve any suitable purpose. For example, in some embodiments needle feature 70 provides the needle with a proximal engagement, or a surface that is configured to interact with a notch shield 80 of the intravascular device 100 (described hereinafter).

The needle feature may comprise any suitable component that has at least one surface that extends laterally past the needle's OD and which is adapted to act as a proximal engagement. Some examples of suitable cannula features comprise one or more crimp features, ferrule features, protuberances, one-way barbs, laterally extending members (e.g., a ring), and other components that have a laterally extending surface. By way of non-limiting illustration, FIG. 11 shows an embodiment in which the needle feature 70 comprises a crimp.

In some embodiments, intravascular device 100 further comprises a notch shield 80 which is at least partially positioned within slit or opening 32 of septum 30. Notch shield 80 generally comprises a tubular structure having an inner lumen through which a portion of the elongate tubular shaft 16 of needle 10 is slidably positioned. In some embodiments, an inner diameter of notch shield 80 is configured to be greater than an outer diameter of shaft 16, yet less than the outer diameter of needle feature 70. Accordingly, as needle 10 is drawn through needle shield 80 in a proximal direction 90, a proximal surface 72 of needle feature 70 makes contact with needle shield 80 thereby positioning notch feature 20 within the inner lumen of notch shield 80, as shown in FIG. 12. Upon further withdrawal of needle 10 in the proximal direction 90, needle feature 70 displaces needle shield 80 from opening 32 of septum 30, thereby entirely removing notch shield 80 and needle 10 from septum 30, as shown in FIG. 13.

In some embodiments, needle feature 70 is provided in a position proximate to needle notch 20 and interposed between needle notch 20 and needle tip 12. Accordingly, at the point in which proximal surface 72 contacts needle shield 80, notch feature 20 is entirely positioned within needle shield 80. Thus, notch shield 80 prevents contact between notch feature 20 and septum 30. In other words, in some embodiments a feature is provided wherein a notch shield is provided for preventing a portion of the septum (such as one or more of the septum leaves) from substantially penetrating the notch feature. Further, in some embodiments notch shield 80 prevents exposure to liquids (such as blood) which may leak from notch feature 20 following a catheterization procedure.

The present invention may be embodied in other specific forms without departing from its structures, methods, or other essential characteristics as broadly described herein and claimed hereinafter. All of the described embodiments and examples are to be considered in any and all respects as illustrative only, and not restrictive. The scope of the invention is, therefore, indicated by the appended claims, rather than by the foregoing description. All changes that come within the meaning and range of equivalency of the claims are to be embraced within their scope.

The invention claimed is:

1. An intravascular device, comprising:
   a catheter adapter having an inner surface and an outer surface;
   a cannula having a notch for providing a flashback signal; and
   a septum having an opening defined by at least three leaves, each leaf having an apex, the septum being seated within the inner surface of the catheter adapter at an axial orientation with respect to an axial orientation of the cannula such that when the cannula is pulled back through the septum, an axial orientation of the notch is misaligned with the axial orientation of the apex of each leaf.

2. The device of claim 1, wherein the notch comprises a plurality of notches and wherein the apex of at least one leaf contacts a portion of the outer surface of the cannula which is interposed between the plurality of notches.

3. The device of claim 1, wherein each leaf is connected to another leaf at a corner, and wherein the notch is aligned with one of the corners.

4. An intravascular device, comprising:
- a catheter adapter having an inner surface and an outer surface;
- a septum seated within the inner surface of the catheter adapter thereby dividing a lumen of the catheter adapter into a proximal chamber and a distal chamber, the septum having an opening defined by a plurality of leaves;
- a cannula having a notch for providing a flashback signal and a needle feature positioned between a tip of the cannula and the notch, the needle feature comprising a portion of the cannula that has an expanded outer diameter; and
- a notch shield positioned around a portion of the cannula, the notch shield having an inner diameter greater than the outer diameter of the cannula and less than the expanded outer diameter of the needle feature, the notch shield being positioned within the opening of the septum while the notch is positioned distally from the opening, wherein upon withdrawing the cannula in a proximal direction, the notch is drawn into the notch shield, whereafter the needle feature contacts a distal surface of the notch shield thereby displacing the notch shield from the opening of the septum in a proximal direction to allow the septum to close.

5. The device of claim 4, wherein the notch shield remains positioned overtop the notch after the cannula has been withdrawn from the septum.

6. The device of claim 4, wherein the needle feature comprises a crimp.

7. The device of claim 4, wherein the needle feature is positioned such that when the needle feature contacts the distal surface of the notch shield, the notch shield covers the entire notch.

8. The device of claim 4, wherein the notch shield prevents blood from exiting from the cannula through the notch after the notch shield is positioned overtop the notch.

9. An intravascular device, comprising:
- a catheter adapter having an inner surface and an outer surface;
- a septum seated within the inner surface of the catheter adapter, the septum having an opening defined by at least three leaves, each leaf having an apex with a thickness; and
- a cannula having a notch for providing a flashback signal, the notch comprising an opening having a length, wherein the length of the opening is less than the thickness of the apex of each leaf thereby preventing the apex from substantially penetrating the notch.

10. The intravascular device of claim 9, wherein the length of the opening is defined along the length of the cannula.

11. The intravascular device of claim 9, wherein the length of the opening is defined around the circumference of the cannula.

12. The intravascular device of claim 9, wherein the cannula has more than one notch, each notch comprising an opening having a length that is less than the thickness of the apex of each leaf.

* * * * *